(12) United States Patent
Hirata

(10) Patent No.: US 8,447,415 B2
(45) Date of Patent: May 21, 2013

(54) CAPSULAR DEVICE FOR ESTHETIC AND THERAPEUTIC BODY TREATMENT

(76) Inventor: Mario Hirata, São Paulo (BR)

( * ) Notice: Subject to any disclaimer, the term of this patent is extended or adjusted under 35 U.S.C. 154(b) by 220 days.

(21) Appl. No.: 12/774,853

(22) Filed: May 6, 2010

(65) Prior Publication Data

US 2010/0286752 A1 Nov. 11, 2010

(30) Foreign Application Priority Data

May 6, 2009 (BR) ...................................... 0901668

(51) Int. Cl.
*A61H 23/00* (2006.01)
*A61H 33/06* (2006.01)
(52) U.S. Cl.
USPC ................................ 607/100; 607/81; 607/96
(58) Field of Classification Search
USPC ........................................................ 607/100
See application file for complete search history.

(56) References Cited

U.S. PATENT DOCUMENTS

| | | | | | |
|---|---|---|---|---|---|
| 2,676,596 | A | * | 4/1954 | Rouat | 607/91 |
| 5,645,578 | A | * | 7/1997 | Daffer et al. | 607/91 |
| 6,272,697 | B1 | * | 8/2001 | Park | 4/524 |
| 6,833,553 | B2 | * | 12/2004 | Slingo | 250/504 R |
| 7,237,284 | B2 | * | 7/2007 | Hensley et al. | 5/425 |
| 7,387,337 | B2 | * | 6/2008 | Keegan et al. | 297/256.13 |

FOREIGN PATENT DOCUMENTS

BR PI 9705982-0 8/1999

* cited by examiner

*Primary Examiner* — Linda Dvorak
*Assistant Examiner* — Jared W Pike
(74) *Attorney, Agent, or Firm* — B. Aaron Schulman, Esq.; Stites & Harbison PLLC

(57) ABSTRACT

A capsular device for esthetic and therapeutic treatment of a patient with emission of infrared together with negative ions, allowing easy elimination of toxins, heavy metals, preventive control of diseases and postsurgical therapeutic treatment.

6 Claims, 5 Drawing Sheets

CAPSULAR DEVICE FOR ESTHETIC AND THERAPEUTIC BODY TREATMENT

FIELD OF THE INVENTION

This invention involves a capsular device for esthetic and therapeutic treatment, but particular involves a device for body treatment.

BACKGROUND OF THE INVENTION

As is widely known, esthetic medicine allows body harmony, that is, esthetic treatment together with medicinal treatment of the body. There are currently several types of treatments that use diversified techniques and devices for body harmony.

One of the simplest esthetic treatment techniques existing in the market is lymphatic drainage, which consists of specific massaging that drains the edema to the lymphatic vessels where it is excreted by the urine.

The esthetic devices most used in treatment clinics or esthetic centers are those of mesotherapy, which consists of applying drugs or cosmetics/special compounds in the skin or subcutaneous skin, allowing reduction of localized fat. However, application in large areas, such as abdomen, back, legs, among others, will not have complete results, since the drug's application has a limit to prevent toxicity.

Another device existing in the market for esthetic/therapeutic treatment consists of thermotherapy, which uses esthetic and phytotherapeutic procedures to treat lipodystrophy and specific pathologies. Said equipment is made up of a heat blanket, equipped with electrical resistances that allow heating of the inner surface of the blanket, promoting elimination of toxins, muscular relaxation, weight loss, skin moisturizing, among others.

However, the inconvenience of said heat blanket resides in the fact that its constructive structure is completely different from the equipment intended herein and does not have a control panel to analyze and diagnose sudden changes in the patient's metabolism, allowing occurrence of emergency situations without the control of the expert, much less show deposit/reservoir contained in the equipment claimed herein, which aims at keeping/collecting the sweat eliminated by the patient for conduction of clinical tests.

Another method of esthetic treatment widely used consists of the application of infrared rays on the body surface, activating the organism's cells, allowing stimulation of deep transpiration and, consequently, elimination of toxins absorbed daily in foods, drinks, polluted air, among others, in addition to the production by the organism itself.

BR document No. PI 9705982-0 was found that involved a health aid instrument to improve blood circulation in the human body, which functioned based on finger pressure formed by a cylindrical body and a lower cover inserted in the lower part of the body. A negative ion discharge element is fixed inside the body. Bio-ceramics is formed inside the body and surrounds the outer upper part of the negative ion discharge element. A germanium compound is formed on the bio-ceramics. A permanent magnet is fixed under the negative ion discharge element and a pressure element is fixed in contact with the lower side of the permanent magnet and in direct contact with the skin in the desired treatment area and projects ions and emissive rays.

The inconvenience found in said model resides in the fact that application of the negative ions is manual, rendering even application of the ions throughout the body surface impossible, in addition to having an embodiment different from the equipment claimed herein.

The applicant himself used in the past a capsular equipment for esthetic/therapeutic equipment, with different characteristics and by virtue of its constant use, developed structural and functioning perfections, promoting better results in the respective treatments, up till then nonexistent in the market.

SUMMARY OF THE INVENTION

Figure 1:
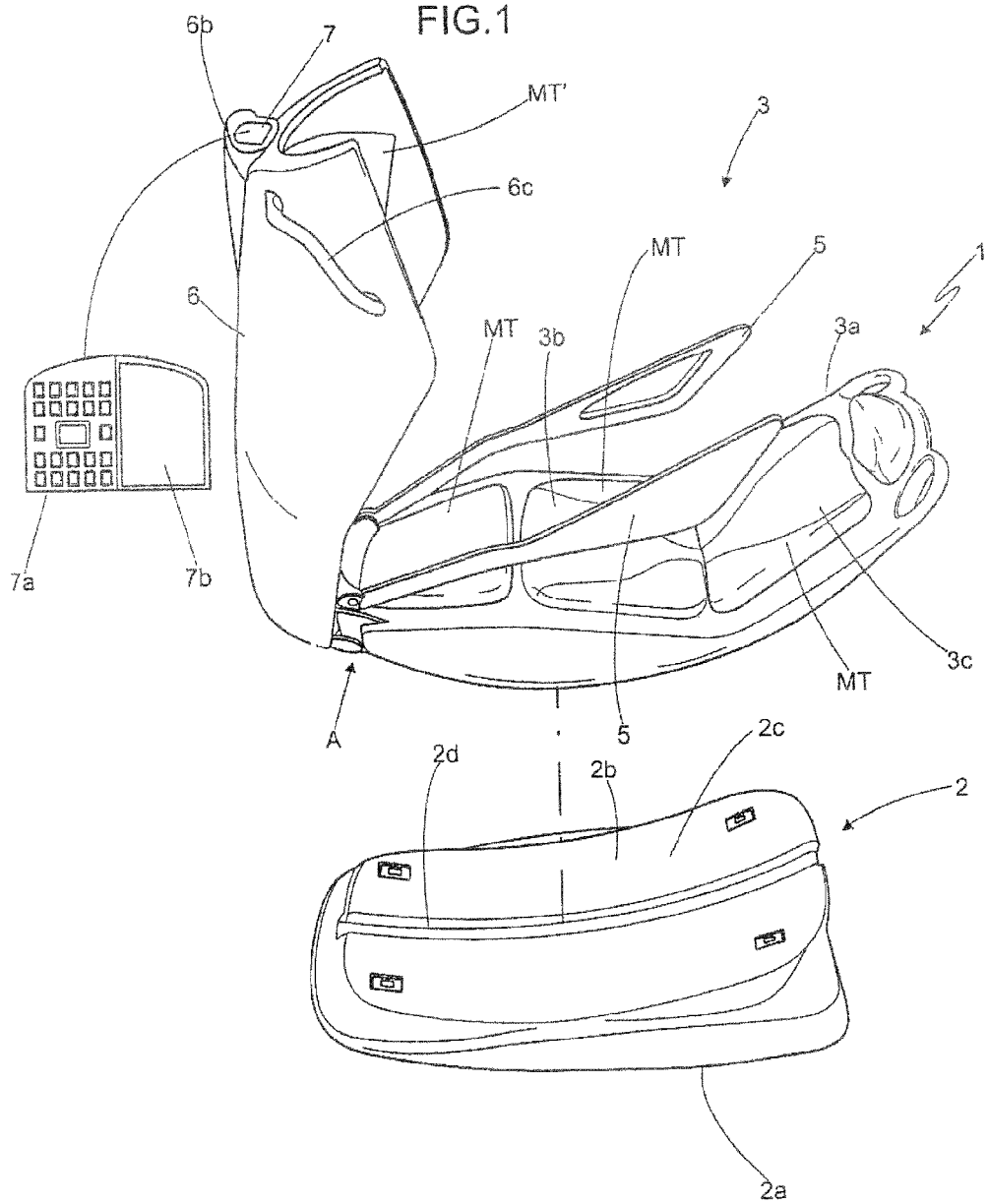
FIG. 1 represents an exploded perspective side view of the capsular device of the structural base showing the cover in open position.
Figure 2:
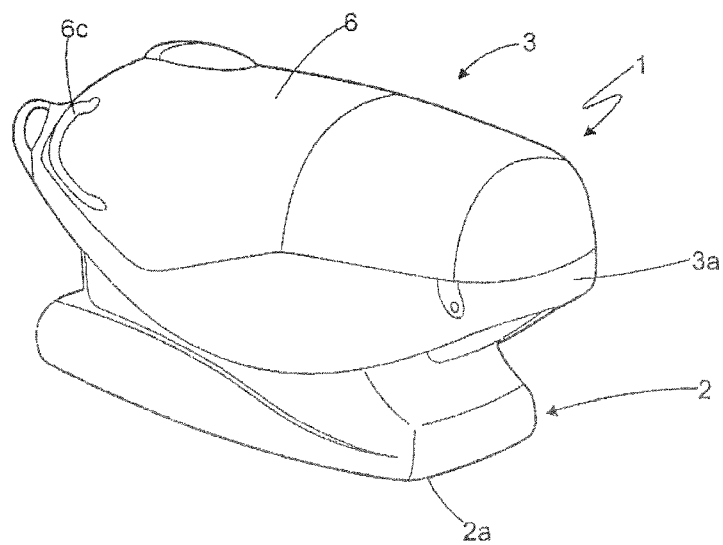
FIG. 2 shows a perspective view of the capsular device in closed position.
Figure 3:
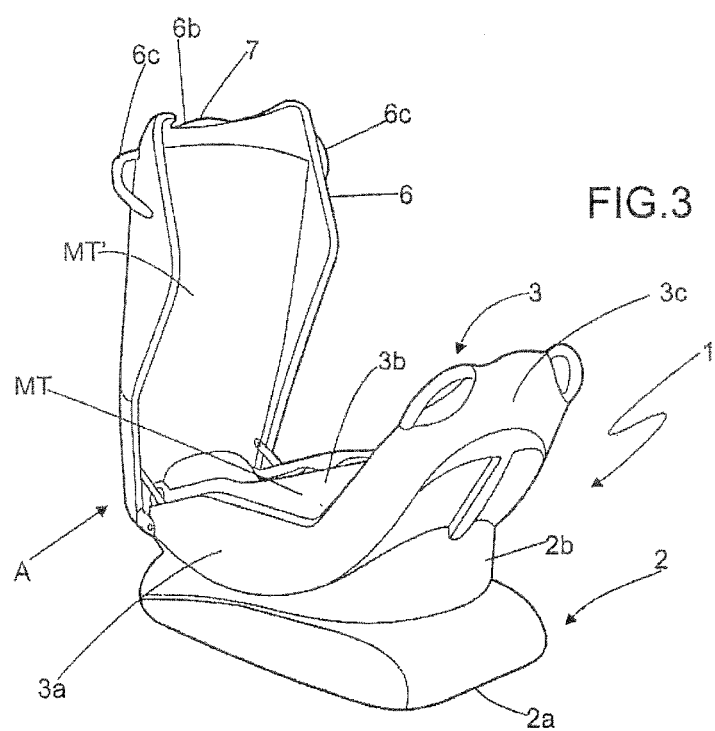
FIG. 3 shows another perspective front view of the device, however, in open position.
Figure 4:
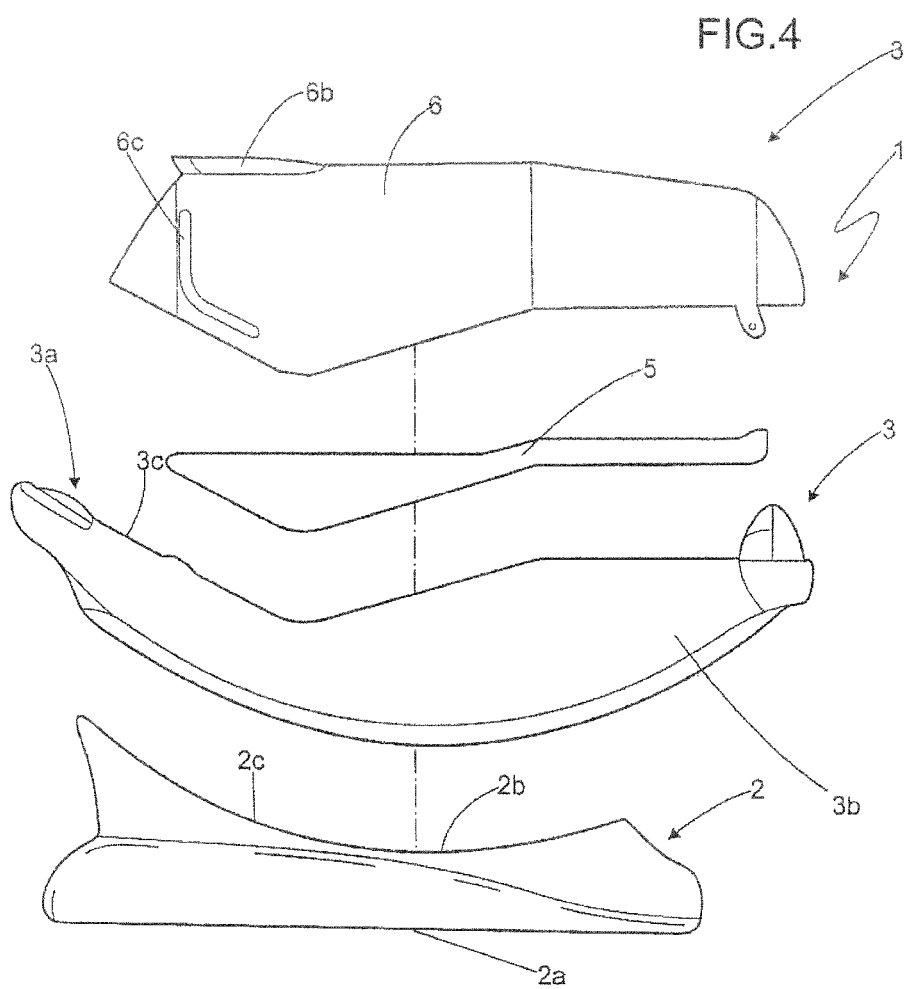
FIG. 4 shows a side view of the capsular device showing the components in schematic explosion.
Figure 5:
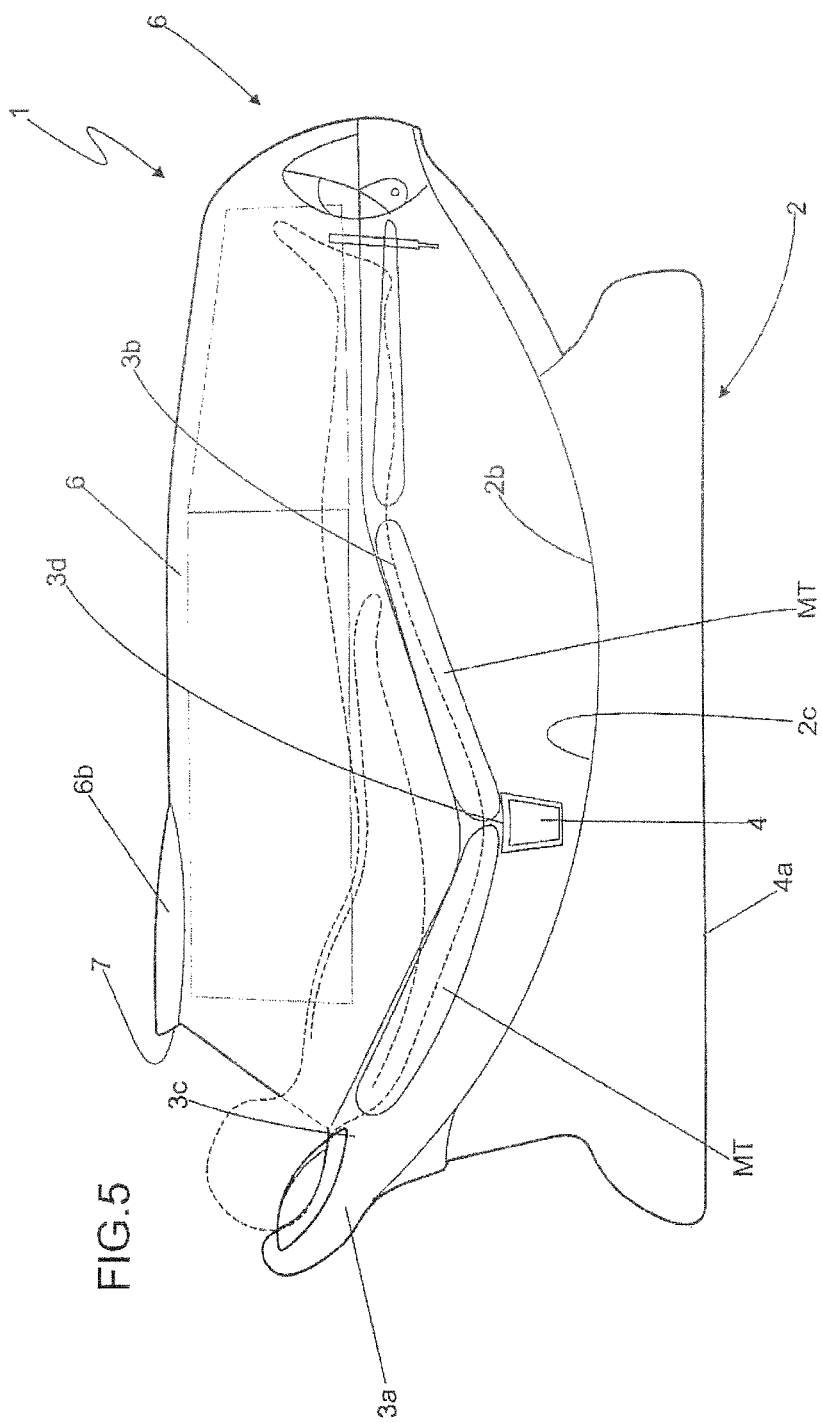
FIG. 5 shows a side view of the device in mounted, closed position and showing, through view in schematic section, the configurations of the innovated device.
Figure 6:
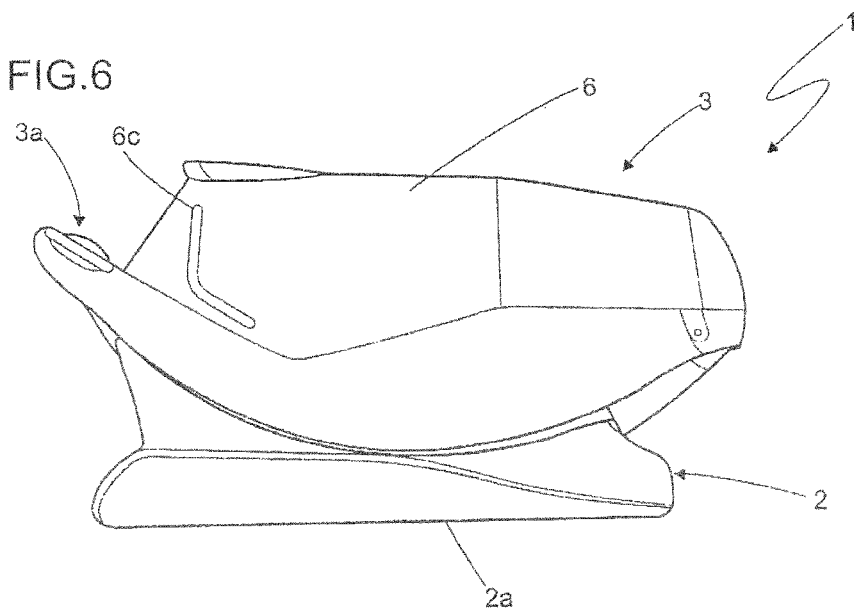
FIGS. 6 and 6A represent side and schematic views of the capsular chamber in resting position and moved almost in the vertical in relation to the lower base.
Figure 6A:
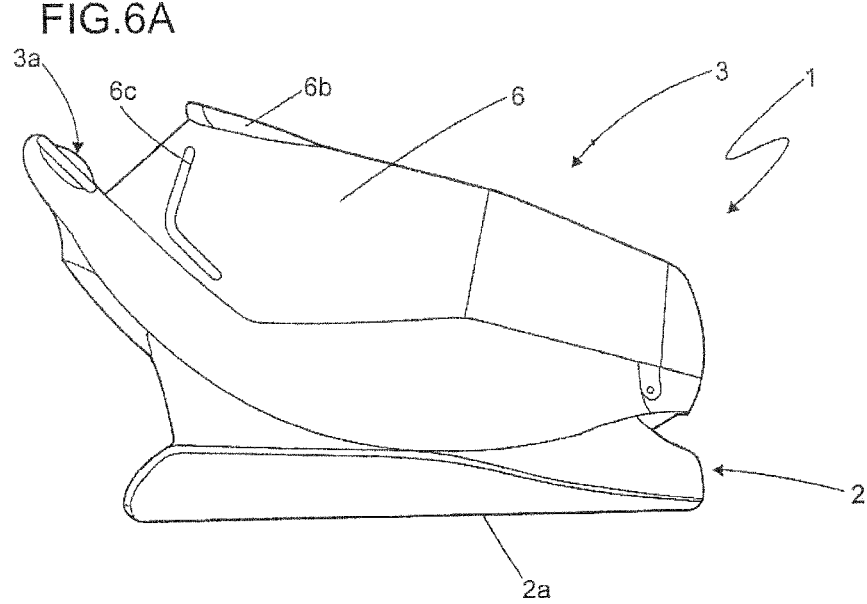

The present application seeks to provide a device for body treatment that promotes benefits for the organism, such as localized weight reduction, neuromuscular treatment, post-surgical liposuction treatment, cellulite reduction, sweat collection for clinical tests, keeping of patient treatment information, among others.

The present Application seeks to provide a capsular device for treatment of the body of a patient, the device comprising a lower structural base and a mobile chamber. The lower structural base comprising a planar lower surface and an upper surface, the upper surface defining a concave arc and being adapted to allow longitudinal sliding movement of the mobile chamber along the concave arc; the mobile chamber being oval and oblong and having a first end and a second end; the mobile chamber comprising an individual base adapted for longitudinal sliding movement along the concave arc of the upper surface of the lower structural base, and an articulated cover pivotally connected to the individual base at the first end of the mobile chamber so as to define an axis of articulation, whereby the articulated cover is adapted to move between an open position, wherein the patient can enter and exit the individual base, and a closed position, wherein the articulated cover contacts the individual base so as to enclose the body of the patient within the mobile chamber.

The individual base comprises a seat, having a seat external surface, the seat external surface being coated with a seat blanket; and a back, having a back external surface; the back external surface being coated with a back blanket, each of the seat blanket and the back blanket being adapted to emit infrared radiation and negative ions when electrically activated; an orifice between the seat and the back, the orifice coupled to a reservoir for collection of sweat from the patient, and at least one protective side arm pivotally connected to the individual base, the at least one protective side arm extending along the length of the seat.

The articulated cover having an outer surface and an internal surface; the internal surface being coated with a cover blanket, the cover blanket being adapted to emit infrared radiation and negative ions when electrically activated, and the outer surface comprising handles and a control panel comprising a computer screen and a patient image screen.

DETAILED DESCRIPTION OF THE INVENTION

Said capsular device is made up of a fixed structural base whose lower surface is a plane, while the opposite surface is made up of a long concave arc where a longitudinal rail is applied, which in turn receives the mobile chamber.

One of the advantages of this equipment resides in its configuration, that is, in its functional design, since said mobile chamber is oval and oblong, allowing the formation of an individual base made up of seat and back, whose interior surfaces are coated by a blanket preferably incorporated with bio-ceramics that, when electrically activated, emits infrared radiation, together with negative ions, allowing acceleration of toxin and heavy metal elimination, identification and control of some diseases and postsurgical therapeutic treatment.

Another innovation of this capsular device consists of the fact that, between the back and seat, that is, in the flaring of the base, there is a central orifice, beneath which a reservoir is coupled for collection of sweat from the patient during treatment, allowing sending of this sweat collected for clinical tests to analyze and check for toxins, diseases, etc.

Another innovation is the fact that the device has side arms applied at the end of the individual base, which are applied as protective elements, since they provide physical safety to the patient during entry and exit from the device.

Said device has a control panel with a computer screen in the inner side of the articulated cover. The screen generates images of the patient and the control panel records and stores all the generated images and all the variations in the measurements. This will enable a constant follow-up of the patient's treatment, and storage and maintenance of the information for the patient's therapeutic history.

Another advantage of the capsular device resides in the fact that it facilitates physical access to the individual base, allowing the use physically handicapped, aged, postsurgical patients, among others, due to the design of the equipment, this being one of its orthopedic functions.

Another advantage resides in the fact that the capsular device allows for full asepsis, due to its embodiment and characteristics and ways of fastening its parts and components, in addition to its facilitating design, preventing deposit of virus and bacteria and transmission from one patient to another, through contact and transmission through sweat or skin.

This Application refers to the capsular device for esthetic and therapeutic body treatment, more precisely a device for body treatment (1) that promotes benefits to the organism, such as localized fat reduction, neuromuscular treatment, postsurgical liposuction treatment, cellulite reduction, collection of sweat for clinical tests, keeping of information on the patient's treatment, among others.

Said capsular device (1) is made up of a lower fixed structural base (2) and a mobile chamber (3), layout on said base that has a plane lower surface (2a) for support on the ground, while the upper surface (2b) is slightly concave (2c) and has a central longitudinal rail (2d) that allows coupling and sliding of the individual base (3a) of said mobile chamber that, in complement, is topped by articulated cover (6).

The mobile chamber (3), formed by the individual base (3a) and articulated cover (6), is oval and oblong, where the individual base (3a) is configured by a seat (3b) and back (3c), whose outer surfaces are coated by blanket (MT), preferably incorporated with bio-ceramics, which when electrically activated emits infrared radiation, together with negative ions, allowing elimination of toxins, heavy metals, reduction of some diseases and postsurgical therapeutic treatment.

Between the back (3c) and seat (3b), that is, in the flared plane of the individual base (3a), there is an orifice (3d) where a reservoir (4) is coupled for collection of sweat from the patient, which once collected is sent for analysis through clinical tests to check for toxins, diseases, etc.

From the end of the individual base (3), near the point of articulation (A) with the cover (6), two protective side arms (5) extend along the length of the seat (3b), which can be articulated in the same axis of articulation (A), guaranteeing access of the patient to the individual base and his or her physical safety (3a).

The articulated cover (6) has an oblong shape, following the format of the base (3a), with a preferably semicircular section, whose internal surface is coated with a blanket (MT') similar to the blanket (MT).

The outer side of said cover (6), more specifically at its free end, opposite to the articulation (A) has a tubular elevation (6b), whose end is coupled to a control panel (7), equipped with computer screen (7a) and patient image screen (7b), allowing constant follow of the patient treatment, with recording and maintenance of the images obtained and the variations in the measurements and keeping of the information on the patient's therapeutic history. At the lateral ends of said cover (6), there are handles (6c) to move the cover (6) by the person in charge.

The individual base (3a) can slide on the central longitudinal rail (2d), and can be displaced within an angle of 0 to 70°, which facilitates its use as well as full asepsis of the equipment.

It is certain that when this invention is put into practice, modifications may be introduced by the applicant with regard to certain constructive details and shape, without this implying moving away from the fundamental principles that are clearly substantiated in the claims, it thus being understood that the terminology used had the purpose of description and not that of limiting the applicant.

The invention claimed is:

1. A capsular device for treatment of the body of a patient, the device comprising a lower structural base and a mobile chamber,
   the lower structural base comprising a planar lower surface and an upper surface, the upper surface defining a concave arc and being adapted to allow longitudinal sliding movement of the mobile chamber along the concave arc;
   the mobile chamber being oval and oblong and having a first end and a second end; the mobile chamber comprising an individual base adapted for longitudinal sliding movement along the concave arc of the upper surface of the lower structural base, and an articulated cover pivotally connected to the individual base at the first end of the mobile chamber so as to define an axis of articulation, whereby the articulated cover is adapted to move between an open position, wherein the patient can enter and exit the individual base, and a closed position, wherein the articulated cover contacts the individual base so as to enclose the body of the patient within the mobile chamber;
   the individual base comprising:
      a seat, having a seat external surface, the seat external surface being coated with a seat blanket;
      a back, having a back external surface; the back external surface being coated with a back blanket, each of the seat blanket and the back blanket being adapted to emit infrared radiation and negative ions when electrically activated;
an orifice between the seat and the back, the orifice coupled to a reservoir for collection of sweat from the patient, and
at least one protective side arm pivotally connected to the individual base, the at least one protective side arm extending along the length of the seat;

the articulated cover having an outer surface and an internal surface;
the internal surface being coated with an articulated cover blanket, the articulated cover blanket being adapted to emit infrared radiation and negative ions when electrically activated, and
the outer surface comprising handles and a control panel comprising a computer screen and a patient image screen, wherein the seat blanket, the back blanket and the articulated cover blanket each comprise bio-ceramics.

2. The capsular device according to claim 1 wherein the individual base can be slidingly displaced by an angle of up to 70° along the concave arc of the upper surface of the lower structural base.

3. The capsular device according to claim 1 wherein the upper surface of the lower structural base comprises a longitudinal recess aligned along the concave arc, and the individual base comprises a projection coupled to the longitudinal recess so as to allow longitudinal sliding movement of the individual base along the concave arc.

4. The capsular device according to claim 1 wherein the articulated cover has a semicircular cross section.

5. The capsular device according to claim 1 wherein the at least one protective side arm is pivotable in the axis of articulation.

6. The capsular device according to claim 1 wherein the handles and the control panel are positioned at the second end of the mobile chamber.

* * * * *